(12) United States Patent
Kahn et al.

(10) Patent No.: US 11,766,213 B1
(45) Date of Patent: Sep. 26, 2023

(54) SLEEP MONITORING BASED COMPLIANCE AND EFFECTIVENESS TRACKING ENGINE

(71) Applicants: Philippe Richard Kahn, Santa Cruz, CA (US); Arthur Kinsolving, Santa Cruz, CA (US); Mark Andrew Christensen, Santa Cruz, CA (US); Sonia Lee Kahn, Santa Cruz, CA (US)

(72) Inventors: Philippe Richard Kahn, Santa Cruz, CA (US); Arthur Kinsolving, Santa Cruz, CA (US); Mark Andrew Christensen, Santa Cruz, CA (US); Sonia Lee Kahn, Santa Cruz, CA (US)

(73) Assignee: DP Technologies, Inc., Scotts Valley, CA (US)

( * ) Notice: Subject to any disclaimer, the term of this patent is extended or adjusted under 35 U.S.C. 154(b) by 517 days.

(21) Appl. No.: 16/946,077

(22) Filed: Jun. 4, 2020

Related U.S. Application Data

(60) Provisional application No. 62/857,276, filed on Jun. 4, 2019.

(51) Int. Cl.
*A61B 5/00* (2006.01)
*G16H 50/70* (2018.01)
(Continued)

(52) U.S. Cl.
CPC .......... *A61B 5/4818* (2013.01); *A61B 5/4815* (2013.01); *A61B 5/747* (2013.01);
(Continued)

(58) Field of Classification Search
CPC ..... A61B 5/4818; A61B 5/4815; A61B 5/747; A61B 2562/0219; A61B 2562/0247;
(Continued)

(56) References Cited

U.S. PATENT DOCUMENTS

| 9,968,293 | B1* | 5/2018 | Kahn | A61B 5/11 |
| 2013/0054215 | A1* | 2/2013 | Stubna | G16Z 99/00 703/11 |

(Continued)

OTHER PUBLICATIONS

Leppanen, Timo, et. al, "Length of Individual Apnea Events is Increased by Supine Position and Modulated by Severity of Obstructive Sleep Apnea," Sleep Disorders, vol. 2016, Article ID 9645347 (13 pages).

*Primary Examiner* — Eric F Winakur
*Assistant Examiner* — Jonathan Drew Moroneso
(74) *Attorney, Agent, or Firm* — Nicholson De Vos Webster & Elliott LLP; Judith Szepesi

(57) ABSTRACT

A compliance and effectiveness tracking engine system including a sensor system to obtain sensed sleep data for a sleep session for a user, and a user interface implementing a user data acquisition system to obtain perceived sleep data from the user after the sleep session. The system further includes a server system implementing a predictive engine to predicted sleep data for the user, based on user background data and transactional data reflecting one or more medical interventions for the user. The server implementing a compliance and effectiveness tracking engine (CETE) to compare the sensed sleep data, the perceived sleep data, and the predicted sleep data, and to determine effectiveness of the one or more medical interventions for the user, and compliance with a protocol associated with the one or more medical interventions.

20 Claims, 11 Drawing Sheets

(51) Int. Cl.
  *G16H 50/30* (2018.01)
  *G16H 50/20* (2018.01)
  *G16H 40/63* (2018.01)
  *G16H 10/60* (2018.01)
  *G16H 20/40* (2018.01)

(52) U.S. Cl.
  CPC ............ *G16H 10/60* (2018.01); *G16H 20/40* (2018.01); *G16H 40/63* (2018.01); *G16H 50/20* (2018.01); *G16H 50/30* (2018.01); *G16H 50/70* (2018.01); *A61B 2562/0219* (2013.01); *A61B 2562/0247* (2013.01)

(58) Field of Classification Search
  CPC ........ G16H 10/60; G16H 20/40; G16H 40/63; G16H 50/20; G16H 50/30; G16H 50/70
  See application file for complete search history.

(56) References Cited

U.S. PATENT DOCUMENTS

| | | | |
|---|---|---|---|
| 2014/0194793 A1* | 7/2014 | Nakata | G01S 13/825 601/48 |
| 2015/0148621 A1* | 5/2015 | Sier | A61B 5/7296 600/595 |
| 2018/0110960 A1* | 4/2018 | Youngblood | A47C 21/048 |
| 2020/0367810 A1* | 11/2020 | Shouldice | A61B 5/4818 |

\* cited by examiner

SLEEP MONITORING BASED COMPLIANCE AND EFFECTIVENESS TRACKING ENGINE

RELATED APPLICATION

The present application claims priority to U.S. Provisional Patent Application No. 62/857,276, filed on Jun. 4, 2019, and incorporates that application by reference in its entirety.

FIELD

The present invention relates to sleep monitoring, and more particularly to a compliance and effectiveness tracking engine based on sleep monitoring data.

BACKGROUND

Pain management is a difficult issue, with many of the medications being addictive. Additionally, many of the medications are valuable on the street. Thus, there is a real risk with over-prescription which can lead to both addition and illegal resale of such drugs. The risk of under-prescription is that patients remain in pain. Therefore, doctors have to walk the fine line of providing sufficient medication for pain management but not enough to encourage overuse and addiction or enable resale. In general, the only way to monitor a patient's medication use is via self-reporting or blood tests. Self-reporting can be manipulated, and blood tests are expensive and uncomfortable.

BRIEF DESCRIPTION OF THE FIGURES

The present invention is illustrated by way of example, and not by way of limitation, in the figures of the accompanying drawings and in which like reference numerals refer to similar elements and in which.

DETAILED DESCRIPTION

The present system in one embodiment obtains useful data from a user who has a painkiller or sleep enhancement medical prescription, or medical intervention, by providing real-time monitoring of the user's sleep. The present system in one embodiment provides effectiveness tracking for prescriptions, as well as other medical interventions such as surgical intervention, mechanical intervention, implanted medical device intervention, etc. By comparing data from a sleep monitoring system, self-reported data, and/or predicted data, the system can determine the compliance level of the user and the effectiveness of the intervention. In this context, compliance level defines the consistent use of a prescribed medication or use of another type of intervention, in accordance with the user's prescription or instructions. The results of the analysis can be used to adjust prescription availability, as well as provide actionable insights to the user, and potentially to the medical provider, and the drug or medical device manufacturer.

In one embodiment, the system may also utilize a background check which may be incorporated into the evaluation. In one embodiment, the system also obtains healthcare transactional data. In one embodiment, the healthcare transaction data includes the history of prescriptions filled, unfilled, frequency, abuse, etc.

In one embodiment, the compliance and effectiveness tracking engine gives the person actionable insights for improving visibility into their body's reactions to their medication and other interventions, and therefore a chance to get a correct prescription for opioids for chronic or other pain management, or appropriate medical interventions for breathing issues. In one embodiment, the system provides a dashboard to enable the doctor or other prescriber to have an outline of all the above for the patient, at a glance. In one embodiment, the system provides an option to drill down to additional detail for an individual patient. The drill-down may include providing sensor data to the prescriber, or their supervisor.

The following detailed description of embodiments of the invention makes reference to the accompanying drawings in which like references indicate similar elements, showing by way of illustration specific embodiments of practicing the invention. Description of these embodiments is in sufficient detail to enable those skilled in the art to practice the invention. One skilled in the art understands that other embodiments may be utilized and that logical, mechanical, electrical, functional and other changes may be made without departing from the scope of the present invention. The following detailed description is, therefore, not to be taken in a limiting sense, and the scope of the present invention is defined only by the appended claims.

Figure 1A:
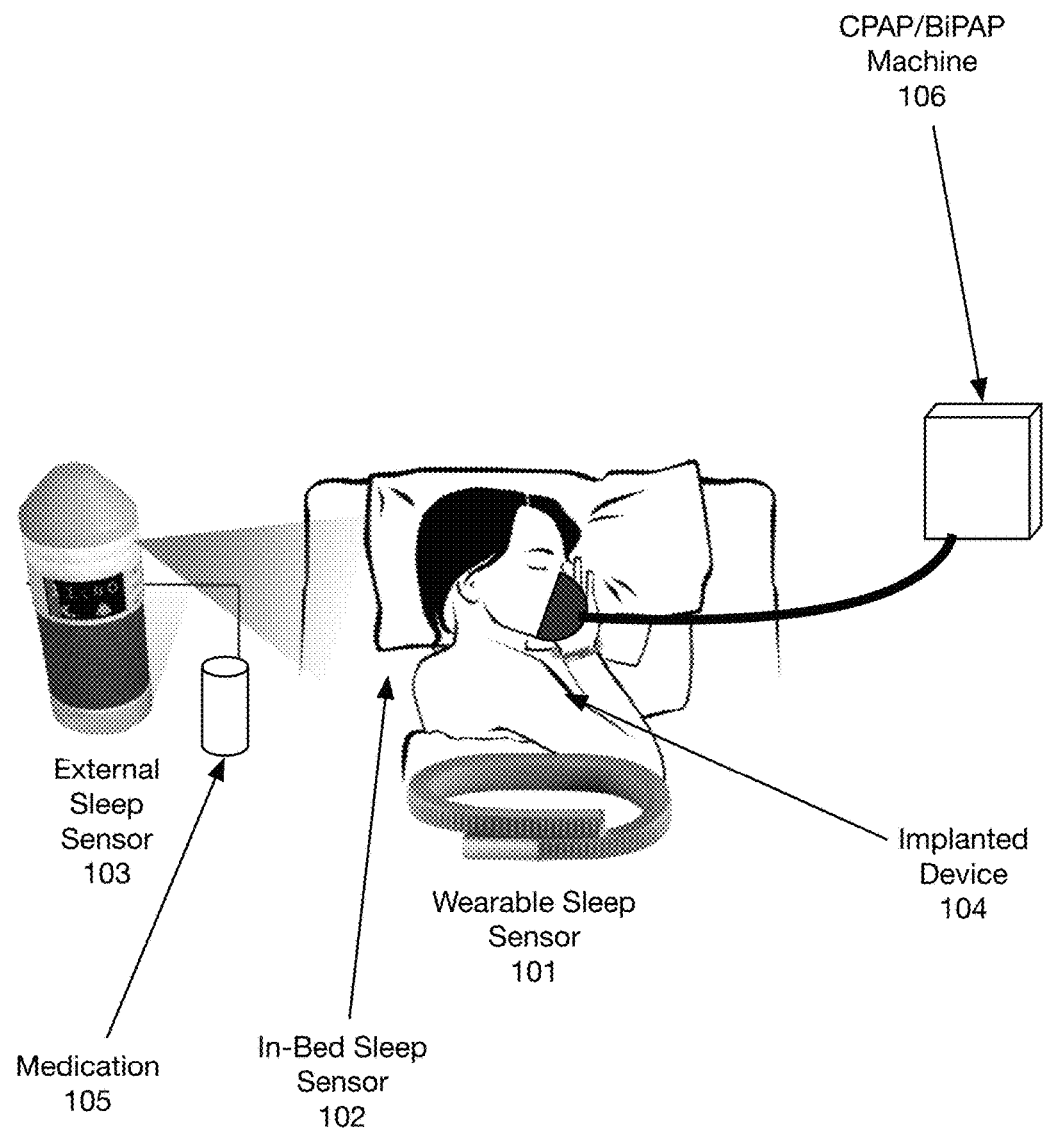
FIG. 1A is an overview illustration of the system.

FIG. 1A is an overview illustration of the system. The sleeper is monitored by one or more sleep sensors. The illustration shows three different sleep sensors. In one embodiment, the sleep sensor is a wearable sleep sensor 101. The wearable sleep sensor 101 may be a watch, a wrist band, an arm band or another type of wearable device. The wearable sleep sensor 101 may be an accelerometer and/or gyroscope in one embodiment. In one embodiment, the sleep sensor may be an in-bed sleep sensor 102. The in-bed sleep sensor 102 may be in the bed frame, in the mattress, in a mattress topper, or in a pillow. The in-bed sleep sensor 102 may be a pressure sensor, in one embodiment. In one embodiment, the sleep sensor may be an external or night stand sleep sensor 103, which is not in contact with the sleep surface or the user. The night stand sleep sensor may be positioned in proximity to the sleep surface to monitor the user, without contact with either the sleep surface or the user. The night stand sleep sensor 103 may be a camera or a passive sensor, in one embodiment. Note that while three separate sleep sensors are shown, in a standard implementation at least one sleep sensor is present. Additionally, another type of sleep sensor may be used.

The sleeper may have one or more medical interventions to improve his or her sleep, and life. In this example, four different interventions are illustrated. One of skill in the art would understand that a standard implementation would have one or more medical interventions, but there is no need for all of these interventions concurrently.

For example, the user may have an implanted device 104, such as the Inspire device from INSPIRE MEDICAL SYSTEMS, INC. Such an implanted device is designed to address sleep apnea, using electric impulses. The present system may be used for monitoring the impact of such a device, and compliance with an activation regimen.

Alternatively, or additionally, the user may be prescribed medication 105. The medication 105 may be one to address an issue that directly impacts sleep, such as apnea, COPD, or asthma. The medication may alternatively be to address other health conditions, but have a possible impact on sleep. The medication 105 may be an opioid in one embodiment. The present system may be used for monitoring the impact of such medication, and compliance with a use regimen.

Alternately or additionally, the user may be prescribed a breathing apparatus, such as a CPAP/BiPAP machine 106. A CPAP (continuous positive airway pressure) machine provides breathing support during sleep. Generally CPAP machines 106 utilize a mask worn by the user. BiPAP machines (Bilevel Positive Airway Pressure) provides breathing support as well, but instead of continuous pressure they adjust to breathing in and out with different pressure levels. The present system may be used for monitoring the impact of such a device, and compliance with a use regimen.

Alternatively, or additionally, the user may have surgery to adjust their breathing (not shown). For example, the user may have a nasal implant from ENTELLUS MEDICAL®. The present system may be used for monitoring the impact of such a device over time.

In one embodiment, the system is designed to be used over time, so that the user's breathing and sleep quality can be monitored pre-intervention and post-intervention. The ability to provide long-term analytics and feedback is useful to the user, the user's medical provider, as well as to the manufacturer of the intervention.

The present system's compliance and effectiveness tracking engine provides, over time, real-world data about the impact of various types of medical interventions on the user's sleep and health. While user verbal feedback is useful, and doctor visits provide information, sleep monitoring provides an unmediated view into the user's state over time, and its changes. The present system thus provides useful feedback to the user, assistance in adjusting prescriptions and monitoring patients to a doctor or medical provider, and continuous feedback over time to manufacturers and distributors of various medical interventions. In this way, the present system provides an integrated way to continue monitoring and optimizing outcomes for the user, as well providing data for a machine learning system which can be used to provide recommendations for others.

Figure 1B:
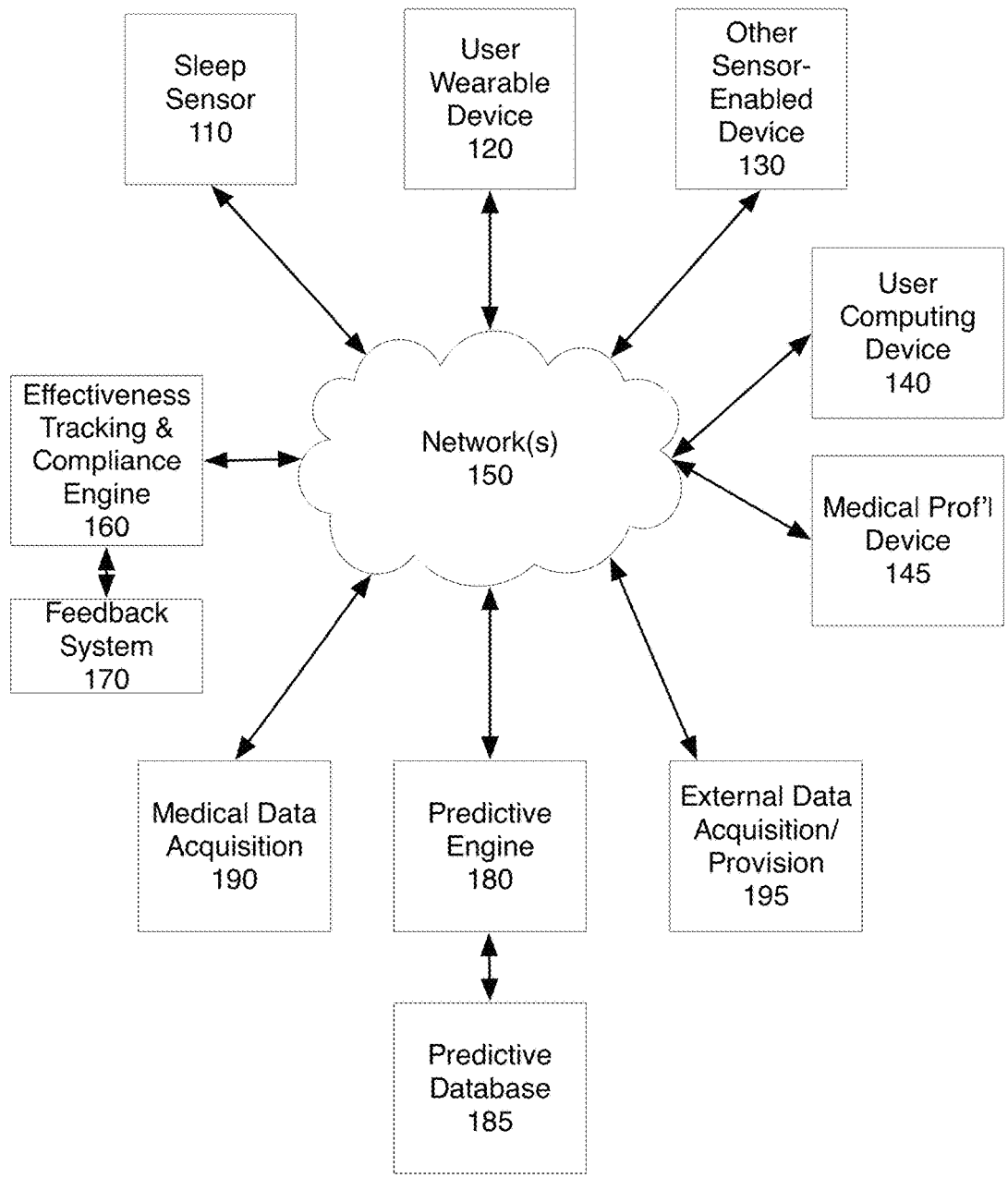
FIG. 1B is system diagram of one embodiment of the elements that may work with a compliance and effectiveness tracking engine.

FIG. 1B is system diagram of one embodiment of the elements that may work with a compliance and effectiveness tracking engine. In one embodiment, the system includes a sleep sensor 110, a user wearable device 120, and/or other sensor-enabled device(s) 130. One or more of these devices are used to obtain sleep data for the user. In one embodiment, the sleep data may include the user's sleep score, waking and sleeping times, sleep duration, deep and REM sleep ratios, wake-ups, and any other aspects of the user's sleep data that the analytics system can determine. In addition to sleep data, the system may also obtain other data if the user has a wearable device, such as movement data throughout the day. In one embodiment, the other sensor enabled devices 130 may include one or more of a mobile device or Bluetooth headset including one or more sensors.

User computing device 140 provides the user with the ability to enter data to the system, and receive alerts or other information in one embodiment. The user computing device 140 may include one or more of: mobile phones, tablets, laptops, and desktop computers. In one embodiment, the user computing device 140 may provide access to a website, or an application which can be used to interact with the present system.

In one embodiment, a user questionnaire is provided through the user computing device 140. The user in one embodiment is asked to put in any medication they took, as well as their sleep report. If the user is utilizing another type of intervention, any settings associated with that intervention are either obtained directly from the device or via user input. In one embodiment, the sleep report includes when the user went to sleep, when they woke up, how often they woke in the night, and how restful the sleep was overall. In one embodiment, the data may also include the user's pain rating if they are taking pain control medication. This "perception data" from the user is compared with the "objective sleep sensing data" obtained from analysis of the data from sleep sensor 110. The combination of perception data and objective data together is used to analyze the effectiveness and use of the medication or other medical intervention.

In one embodiment, the data may also be analyzed in light of objective healthcare transactional data. Healthcare transactional data includes the prescriptions received by the user, unfilled prescriptions, frequency of medications, a history of abuse, a history of diseases and/or injury or other triggers for needing pain management, and other medical interventions. In one embodiment, the system only receives prescription data from the user, which is validated by a medical professional, rather than receiving Healthcare Insurance Portability and Accountability Act (HIPAA) regulated data from a medical provider. In another embodiment, the system receives HIPAA-regulated data from the medical provider(s) of the user, and ensures that such data is securely stored. Furthermore, in one embodiment, data which is provided to the predictive engine 180 is sufficiently abstracted to ensure that it includes no personally identifiable data.

Compliance and effectiveness tracking engine 160 utilizes the perception data from the user via device 140, the objective sensor data from sensors 110, 120, 130, and when available, medical data from medical data acquisition 190 or from the user. Compliance and effectiveness tracking engine 160 determines the user's level of compliance with prescription or medical intervention associated behaviors. Compliance and effectiveness tracking engine 160 also in one embodiment, tracks the effectiveness of the medical intervention for the user.

Feedback system 170 provides feedback about the user's compliance level and the effectiveness of the intervention. In one embodiment, the feedback system 170 provides actionable recommendations and data to the user. In one embodiment, the feedback system 170 provides data to a medical professional, via a medical professional device 145. The device 145 may utilize an application, or access to a website or other data source. In one embodiment, the data provided to the medical professional may be a dashboard, showing the compliance level of a plurality of users/patients. In one embodiment, the feedback system 170 may also provide a recommendation for future prescriptions and/or medical interventions, based on the compliance level. In one embodiment, feedback system 170 may further provide aggregate data to manufacturers and/or distributors about the effectiveness of the intervention for certain demographics.

The predictive database 185 is constructed by the predictive engine 180 using machine learning and artificial intelligence (AI) mechanisms to take the abstracted data from a large number of users and assist in creating the predictive database used by compliance and effectiveness tracking engine.

In one embodiment, external data acquisition system 195 may obtain data from the FDA, medical manufacturers, and others regarding the effects and side-effects of the various drugs and/or medical interventions being monitored. This data may be used by the predictive engine 180 in building the predictive database 185. It may also be used by the compliance and effectiveness tracking engine 160 to determine the expected effects of medications and other medical interventions. In one embodiment, the external data acquisition/provision 195 system may also obtain background check data about the user. Background check data may include addiction history or history of selling medications. This type of data may be used to evaluate the likelihood that the user would misuse the prescription.

In one embodiment, the system may also be used to provide feedback to medical manufacturers. In one embodiment, the adjustments of prescriptions over time may be cumulatively disclosed, with no personally identifiable data. The impact on the sleeping patterns of the users taking medications, or utilizing other medical interventions, may also be disclosed, on a cumulative basis.

In this way, the system obtains objective data from a sleep sensor, objective data regarding a user's medical prescriptions and/or other medical interventions, subjective data from the user, and predictive data, and utilizes this combination of data to evaluate the effectiveness of medication and/or medical intervention for the user, and the compliance level of the user. In one embodiment, the system can use this data to make recommendations to the user and/or the medical provider. This data may also be provided to manufacturers or researchers, as will be discussed below.

Figure 2:
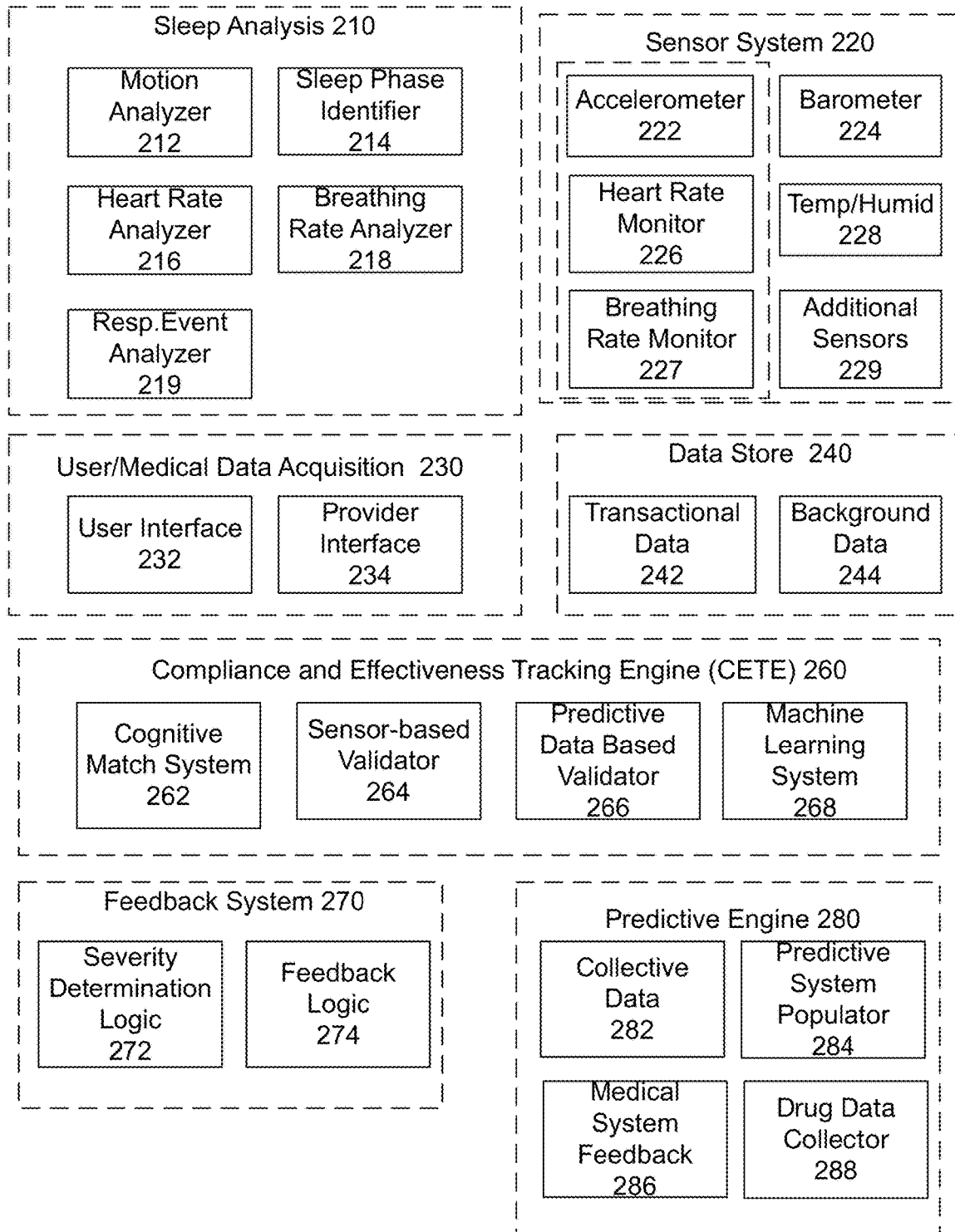
FIG. 2 is a block diagram of one embodiment of the compliance and effectiveness tracking engine system.

FIG. 2 is a block diagram of one embodiment of the compliance and effectiveness tracking engine system. The compliance and effectiveness tracking engine system 206 may include one or more of a sleep analysis system 210, sensors 220, a user/medical data acquisition system 230, data store 240, compliance and effectiveness tracking engine 260, feedback system 270, and predictive engine server 280.

The sensors 220 include one or more sensors for monitoring the user's sleep. In one embodiment the sensors 220 may also include sensors for monitoring the user's movements during the day. In one embodiment an accelerometer 222 or other motion sensor, a heart rate monitor 226, a breathing rate monitor 227 included. In one embodiment, the heart rate monitor 226 and breathing rate monitor 227 are part of the motion sensing system 223. In one embodiment, the motion sensing system is used the heart rate monitor 226 and breathing rate monitor 227. In one embodiment, the motion sensor is a pressure sensor. In one embodiment, the motion sensor 212 is an optical sensor, a pressure sensor, an accelerometer, or a combination of one or more such sensors. In one embodiment, the sensor system includes a microphone for sound detection. The sensor system 220 further includes in one embodiment other sensors such as a barometer 224, temperature and/or humidity sensor 228, and optionally additional sensors 229. In one embodiment, although a single sensor is shown any of these sensors may be multiple sensors. For example, the system may include a pressure sensor embedded in a bed for monitoring sleep, and a separate motion sensor in a wearable device. The wearable device may additionally be used to monitor the user during the day.

The data from the sensor system 220 is passed to the sleep analysis logic 210. The sleep analysis logic 210 in one embodiment includes motion analyzer 212, heat rate analyzer 216, and breathing rate analyzer 218, and respiratory event analyzer 219.

In one embodiment, the heart rate analyzer 216 and/or breathing rate analyzer 218 receive data from sleep analysis system 210 from one or more sensors to identify the heart rate and/or breathing rate.

In one embodiment, respiratory event analyzer identifies respiratory events which indicate that the user is having a hard time breathing. Causes of such respiratory events include sleep apnea, chronic obstructive pulmonary disease (COPD), and asthma. In one embodiment, the respiratory event analyzer 219 determines the cause of the respiratory event and its severity. In some embodiments for severe respiratory events the system may have an alarm to wake the user.

In one embodiment, the sleep phase identifier 214 utilizes the data from the sensors to classify the user's sleep phase. In one embodiment, the sleep analysis 210 occurs as the user sleeps, utilizing current sensor data and prior sensor data. In one embodiment, the sleep phase identifier 214 may further determine the user's sleep quality. Sleep quality identifies the length of each sleep phase, restlessness, waking, snoring, any respiratory events, and other aspects of the sleep that influence how effective sleep is in providing rest and refreshment. The sleep phase identifier 214 in one embodiment is implemented by a special purpose processor, which utilizes the combined sensor data to determine the user's sleep data. In another embodiment, the sleep phase identifier 214 may be part of a server or cloud computing environment, and the sleep analysis may take place remotely. In another embodiment, the sleep phase identifier 214 may be implemented by a user computing device, such as a smart phone or computer, which receives the data from the sensor system 220.

In one embodiment, the system further includes user/medical data acquisition 230. The data acquisition 230 in one embodiment includes a website or application providing a user interface 232, enabling the user to input their information. In one embodiment, the user interface 232 enables users to enter their personal medical data, as well as their perceived sleep quality, as will be discussed below. In one embodiment, the user interface 232 presents a questionnaire which may be used by the user. In one embodiment, the user may scan their prescriptions or medical devices. In one embodiment, the data acquisition 230 may also include a provider interface 234, which enables the provider, e.g. the doctor or their staff, to enter data about the patient. In one embodiment, the data may include personal characteristics, prescriptions, medical interventions, and any other relevant diagnostic data.

Transactional data 242 is stored in data store 240. Transactional data includes the particular medicines and dosages prescribed to the user, as well as any other medical interventions and their associated settings. The data store 240 also includes in one embodiment, background data 244 about the user. Background data 244 includes "user characteristic data" and "current user condition data." User characteristic data includes the user's age, gender, fitness, weight, medical history, medical conditions, injuries, etc. In one embodiment, the system includes current user condition data, which may adjust the user characteristics, e.g. recent injuries, temporary health conditions, etc. Background data 244 may also include data from a background check. In one embodiment, the user condition data is regularly updated, while the user characteristic data tends to remain stable (though it too may change). In one embodiment, data store 240 is a secure data storage on a server system. In one embodiment, all data utilized by the system and associated with a user is encrypted, to ensure compliance with privacy requirements.

Compliance and effectiveness tracking engine 260 utilizes the data to determine whether the user is complying with their prescription requirements, and whether the prescribed medication or provided medical intervention is providing the expected benefits, or having any negative side effects.

The system in one embodiment relies on a machine learning system 268 which is an engine trained by predictive engine 280 based on the large set of data from many patients. The machine learning system 268 receives data and inputs, and provides an analysis to identify the user's sleep time and quality. In sleep, users cannot control their motions or movements, nor their waking patterns. Thus, it is an unadulterated reflection of their actual health status, and is more accurate than what is reflected by their behavior while awake, or their statements to a medical professional.

Cognitive match system 262 utilizes feedback directly from the user about their sleep quality, and any sleep events they are aware of. In one embodiment, the cognitive match system 262 associates the user's feedback with the processed sleep data which reflects the user's sleep phases and any detected respiratory events, or sleep events such as waking, snoring, etc. This data is used to provide a preliminary analysis of how well the user slept, and thus how effective the medication or other intervention has been.

Sensor-based validator 264 compares the data from the cognitive match system 262 based on the user's input about their perceived sleep quality and pain management with the sensor data determined by the sleep analysis system 210. While the user's perception can be different than the sensor-observed data this discrepancy is often informative about the user's state and compliance.

Predictive data based validator 266 compares the user's sleep patterns—as determined by the sensor systems—to the expected patterns based on the user's background and prescription/intervention data. For example, if a user is prescribed Ambien, to assist them in falling asleep, and they take the pills the prediction would be that they would likely sleep through the night, but may have more movement. For some opioids, the user may sleep more deeply with a slower sleep cycle. The predictive data utilizes the machine learning system, which may also receive as input medical testing data. This enables the system to compare the observed pattern of the user to the predicted pattern if they are in compliance with the prescription.

Feedback system 270 can be utilized to analyze the user's sleep. In one embodiment, the feedback system 270 may provide some analysis in real time. In one embodiment, the feedback system 270 provides feedback after each sleep session as well. In one embodiment, the severity determination logic 272 determines whether a detected respiratory event or sleep disturbance requires an urgent alert. In one embodiment, for example, an urgent alert may be needed if the user is sleepwalking or having severe sleep apnea. The feedback system 270 may wake the user, if needed. Additionally, the feedback system 270 may notify the doctor, and optionally other appropriate parties about any issues observed. Feedback system may include audio output such as a speaker for an audio alarm. Feedback system may also include a display screen for displaying data, and providing visual feedback.

In addition to the urgent feedback, feedback system 270 provides information about their sleep to the user. In one embodiment, the feedback system 270 may also provide actionable data to the user. For example, the user may receive recommendations such as a suggestion to go to bed at a different time, or alert the time they take their medication, or recommend that they discuss adjusting their CPAP settings with their doctor. The feedback system 270 may also provide feedback to the medical provider, for example suggesting an adjustment in the prescription or medical intervention. In one embodiment, the predictive engine server 280 may utilize the data from a large number users to determine what feedback and suggestions should be made.

Predictive engine 280 uses the stripped data—in which personally identifiable information has been removed—to create a predictive system which is a machine learning system that can be used to provide analysis and recommendations to users and prescribers. In one embodiment, the results determined by the predictive engine 280 may also be provided to manufacturers, and medical systems. In one embodiment, the data may be made available for analysis to medical researchers.

In one embodiment, the compliance and effectiveness tracking engine system 206 is implemented across multiple devices. The sensor system 220 resides in one or more special purpose sensing systems in the area where the user sleeps. The sleep analysis 210 may take place locally to the user, on a special purpose processor, on the user's computing device, or remotely on a server or cloud server systems. Data acquisition may be via a website provided through another server or cloud infrastructure. Compliance and effectiveness tracking engine 260 in one embodiment is implemented on a server which receives data via a network, and generates processed data, which is accessible to the user via the user's device. Predictive engine 280 may be implemented in a separate server system, or distributed system. Feedback system, in one embodiment, may be implemented on a server, with actual feedback provided through an application, a website, an alarm system, or another mechanism.

Figure 3:
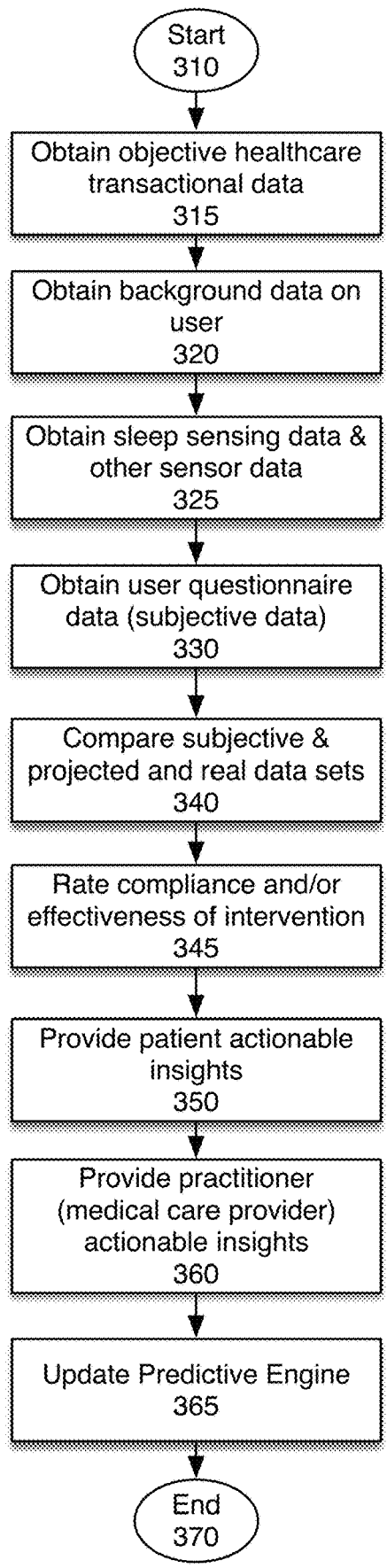
FIG. 3 is an overview flowchart of one embodiment of monitoring compliance.

FIG. 3 is an overview flowchart of one embodiment of monitoring compliance. In one embodiment, the system at block 315 obtains objective healthcare transactional data. this includes the particular medicines and dosages prescribed to the user and any other medical interventions including surgical interventions, the use of CPAP or BiPAP etc.

At block 320, the system obtains background data on the user. The background data includes "user characteristic data" and "current user condition data." User characteristic data includes permanent medical conditions, injuries, age, gender, etc. In one embodiment, the system includes current user condition data, which may adjust the user characteristics, e.g. recent injuries, temporary health conditions, etc. In one embodiment, the user condition data is regularly updated, while the user characteristic data tends to remain stable (though it too may change).

At block 325, the system obtains sleep sensing data. Sleep sensing data utilizes one or more sensors to monitor the user's sleep in real-time, using sensors. The data is then processed to obtain the user's sleep patterns (e.g. when the user goes to sleep, when they wake up, wakefulness periods within a sleep episode), the user's sleep quality (cycles of deep and REM sleep), as well as any other conditions that may impact sleep (such as snoring, apnea episodes, restless legs, breathing issues, etc.). In one embodiment, when additional data is available from other sensors, that is also obtained. Other sensor data may be wearable data, from a device such as a wristband or other sensor which monitors the user when out of bed.

At block 330, user questionnaire data is obtained. In one embodiment, the user is presented with a simple interface that allows them to verify their medical dosage, and rate the quality of their sleep and indicate any waking cycles. This data is subjective. In one embodiment, this data is requested every morning from the user, upon waking.

At block 340, the system compares the subjective and objective data as well as projected data. This determines how closely the user's subjective data matches real-world data, as well as how closely the user's data matches the predicted data based on the user background data, and objective data.

At block 345, the compliance level and/or effectiveness level is rated. The compliance level is determined based in part on how closely the user's sleep pattern matches the expected patterns, and if there are any significant changes observed without a corresponding change in either the user condition data or the user's current prescriptions. The effectiveness level for the medical intervention is rated based on how well the user sleeps, compared to others with similar characteristics and interventions.

At block 350, the system provides patient actionable insights. The patient actionable insights may include recommendations for altering sleep or exercise patterns, or for talking to a medical provider.

In one embodiment, the system provides practitioner actionable insights at block 360. These insights may provide data about the compliance level of the user to a prescribing doctor. In one embodiment, the user data is utilized to update the predictive engine, with additional data. In one embodiment, this data is stripped of all personally recognizable data, and provided to the predictive engine as batched information. The process then ends at block 370.

Of course, though FIG. 3 is shown as a flowchart, in one embodiment the order of the steps is not important except to the extent that one block relies on another. Furthermore, any interaction may use an interrupt driven system. For example in FIG. 3 the order that data is acquired is not relevant. Furthermore processing may be continuous and thus data may be continuously acquired and processed.

Figure 4:
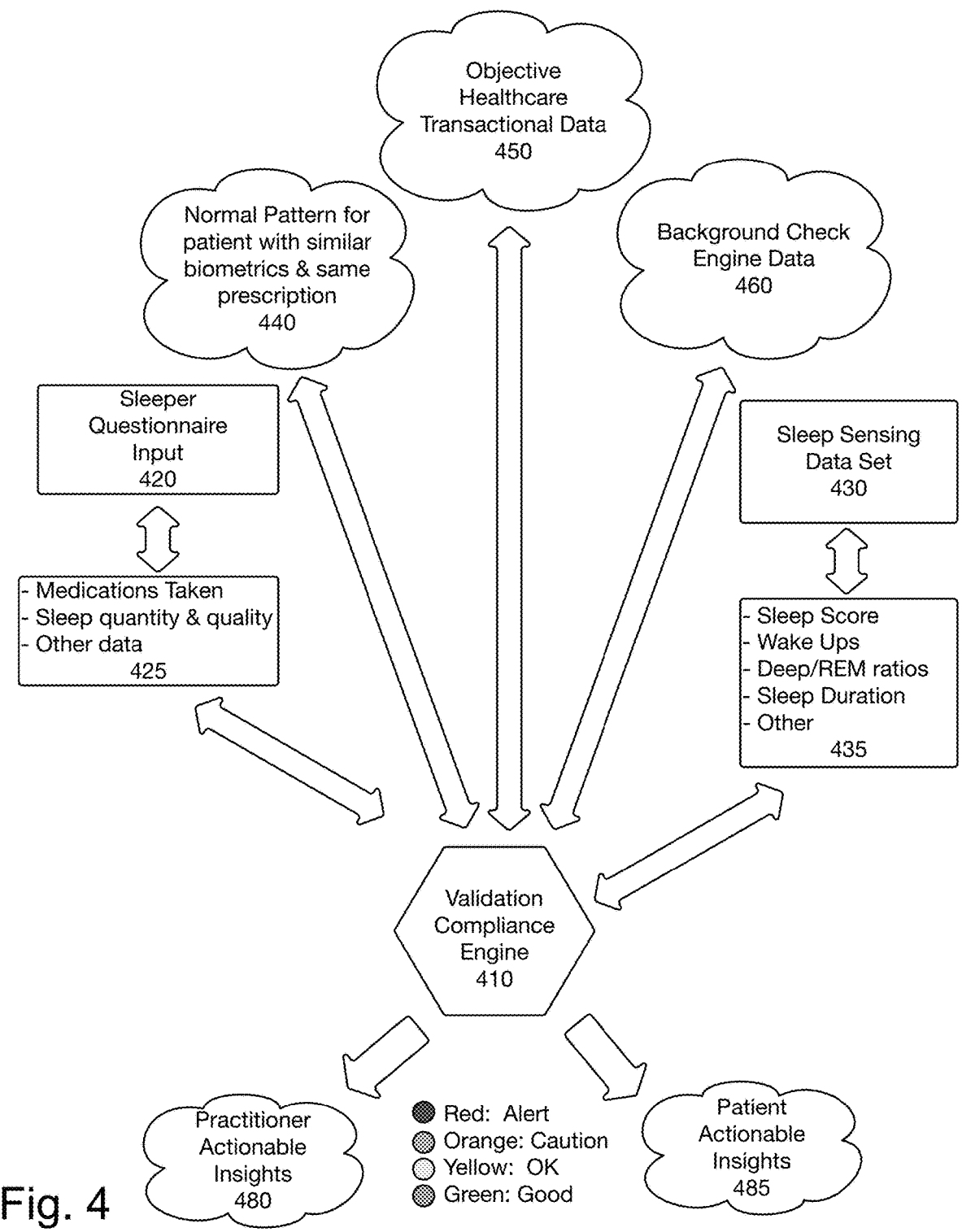
FIG. 4 is an exemplary overview of compliance ratings.

FIG. 4 is an exemplary overview of compliance ratings. In one embodiment, the ratings include good, OK, caution, and alert. In one embodiment, Good rating indicates that the user is compliant with the prescription and their perception data and real-world data match the predictive effect of the medications prescribed. In one embodiment, 80% compliance is considered good. Less than 50% compliance is considered alert-worthy. Note that although this indicates "compliance" it also can be used to evaluate the effectiveness of the medication for the user. In one embodiment, especially when a new prescription is given to a user, the system may be used to evaluate the effectiveness of the new medication, or the new dosage.

In one embodiment, the system evaluates whether the mismatch between prediction and real-world effect of the medication is the result of lack of compliance or the medication not working well for the user. In one embodiment, the system uses the data to predict the effects of changes to the prescriptions of the user. In one embodiment, the system uses the data to predict the effects of changes to other behaviors, for example, changing exercise, sleeping times, etc. In one embodiment, this may be used to provide recommendations to the user, e.g. a recommendation to exercise earlier in the day, to go to bed or wake at a different time, etc. In one embodiment, the analysis system may be used to provide recommendations to the doctor regarding the user, e.g. a recommendation to alter the prescription dosage, an alternative medicine, or a conversation with the patient to improve compliance. In one embodiment, when the user's compliance level is below a certain level the system recommends an appointment with the doctor.

Figure 5:
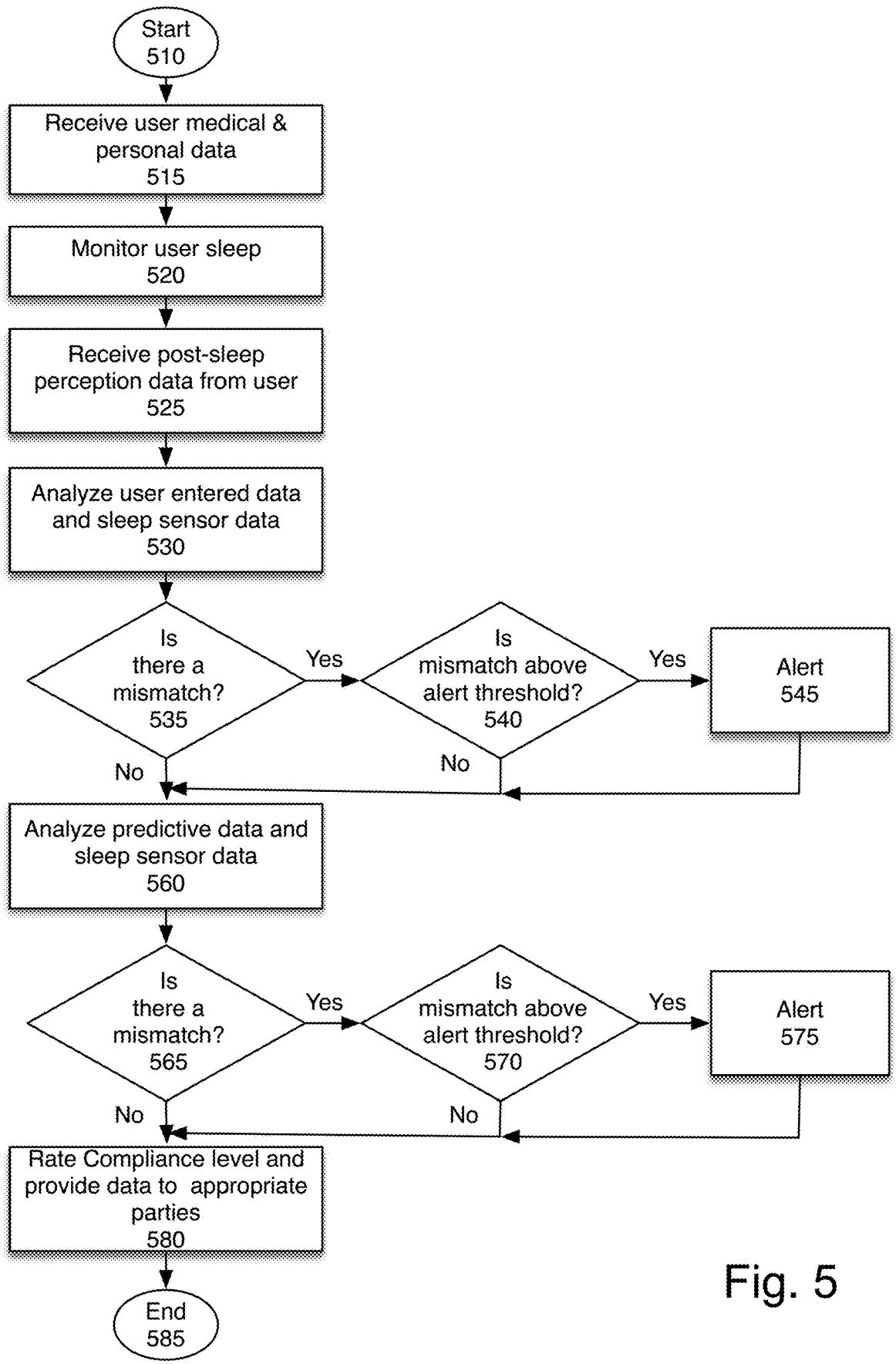
FIG. 5 is a flowchart of one embodiment of sleep monitoring and compliance monitoring.

FIG. 5 is a flowchart of one embodiment of sleep monitoring and compliance monitoring. The process starts at block 510. In one embodiment, the process starts when the user starts utilizing the system.

At block 515, the user medical and personal data for the user is obtained. As noted above, the user may enter this data, the user's medical provider may enter this data, the data may be obtained from third party sources. For example, if the user has a smart scale, their weight and body composition data may be available, or if the user has a health application that has their age, gender, and other data this data may be obtained with the user's authorization. In one embodiment, in addition to the user's personal data, the system also obtains the user's prescription data. The prescription data specifies the medication(s) the user is taking, including the frequency, timing, and amount taken.

At block 520, the user's sleep is monitored. As noted above sleep monitoring may utilize one or more sensors. The sensors in one embodiment may be embedded in the user's bedframe, mattress, mattress topper, and/or pillow. The sensors in one embodiment may be in body-worn devices such as wristbands or watches. The sensors in one embodiment may be non-contact sensors in proximity to the sleep surface, such as cameras or area motion detectors. The data obtained by the one or more sensors are sent to a sleep analysis processor, which utilizes the combination of new data and prior data to analyze the user's sleep. The output of the sleep analysis system, in one embodiment is the user's sleep phase, heart rate, breathing rate, and restlessness level. This data is stored.

At block 525, post-sleep perception data is received from the user. The user in one embodiment is presented with a short questionnaire at the end of the sleep cycle, requesting data about their perceived sleep length, occurrences of waking during the sleep session, and sleep quality. In one embodiment, if the medication being monitored is a pain killer, the user's pain perception is also queried. In one embodiment, an application which is used to monitor the sleep on the user's mobile device prompts entry of this data. In one embodiment, the user must enter this data prior to using the device for other purposes. In one embodiment, if the user does not fill in the perception data, they are reminded frequently after waking. In one embodiment, if the user does not enter the data after a certain period, the reminder may shift to a different medium, e.g. a text or email or phone call may be triggered.

At block 530, the user entered data is matched to the sleep sensor data. In one embodiment, the system evaluates one or more of: the number of perceived awakenings, the time until the user fell asleep, the sleep length, the relative restfulness of the sleep, and the quality of sleep. Other factors may also be compared. In one embodiment, if the user provides relative timing for certain occurrences (e.g. restlessness at 2 a.m.) the system aligns this data with the sleep sensor data.

At block 535, the process determines whether there is a mismatch between the user's perceived sleep experience and the sleep sensor data. If so, the process determines at block

540, whether the mismatch is above an alert threshold. If not, the process continues to block 560.

In one embodiment, if the user's perception is significantly different from the actual data, this becomes of interest. In one embodiment, the mismatch is considered above a threshold if the user perceives that they were awake for a significant portion of time when they sensor data indicates they were asleep, or vice versa. In one embodiment, the threshold is greater than 25% of the time where the user indicates they were in one state, when they were actually in another state. In one embodiment, the mismatch is considered above a threshold when the user perceives that they did not get sufficient restful sleep but the sleep sensor data indicates that they had sufficient deep sleep. In one embodiment if the user indicates that they had less than 50% of the deep sleep they felt they needed, when the sleep sensor data indicates they had sufficient amount, that is above the threshold. Similarly, if the user indicates they had sufficient deep sleep, but the sleep sensor data indicates they had less than 50% of the needed deep sleep, that is above the threshold.

If the mismatch is above the threshold, in one embodiment, at block 545 the system generates an alert. In on embodiment an alert may be a notification to the user that their perceived sleep quality does not match what the sensor has detected. In on embodiment, the alert may include notifying a medical provider. For certain types of mismatches, for example, if the user indicates that they slept but according to the sensor they had not had any deep sleep, a more significant alert may be sent. If the user's sleep pattern indicates an actual danger, the alert may extend to calling emergency services. The process continues to block 560. If there is no mismatch, the process continues directly to block 560.

At block 560, the predictive data and sleep sensor data are analyzed. Predictive data predicts the user's sleep pattern, based on various factors. In one embodiment, the predictive data utilizes the user's age, gender, health conditions, and medication to predict a sleep pattern. In one embodiment for users with prior history, the system may utilize previously collected sleep data to establish the predictive threshold.

At block 565, the process determines whether there is a mismatch. If there is a mismatch and it is above a threshold, as determined at block 570, the process continues to block 757 to alert. Otherwise, the process continues directly to block 580.

In one embodiment, the threshold for a mismatch depends on a number of factors. For a new user, for whom there is no personal predictive data yet, a mismatch would have to be at least two standard deviations from the range of normal sleep patterns for someone with the user's characteristics for it to meet the threshold. In contrast, if the system has the user's own past sleep pattern data for the predictive analysis a deviation by a much smaller amount would be above a threshold. In one embodiment, if the user's medication is changed, the threshold may be adjusted. In one embodiment, for a comparison to a baseline pattern for others similar, the threshold is two standard deviations. In one embodiment for a comparison to the user's own patterns, with no changes in medication or health, the threshold is a 20% change. In one embodiment, for a comparison to the user's own patterns, with a change in medication or health, a 10% change is considered worth alerting. In one embodiment, the medical provider may set the threshold. In one embodiment, the user may set the threshold.

At block 580, the compliance level of the user is rated, based on the mismatches between user perception, real sleep sensor data, and predictive data. In one embodiment, the compliance level may be displayed to the user as one of a red/orange/yellow/green tiers. The process then ends at block 585. On a subsequent uses, the process starts at block 520, monitoring the user's sleep patterns.

Note that although FIG. 5 is in a flowchart format the order of the blocks is not limiting. Thus, while the system is illustrated as a flowchart it is not ordered, except to the extent that subsequent parts of the method are dependent on each other.

Figure 6:
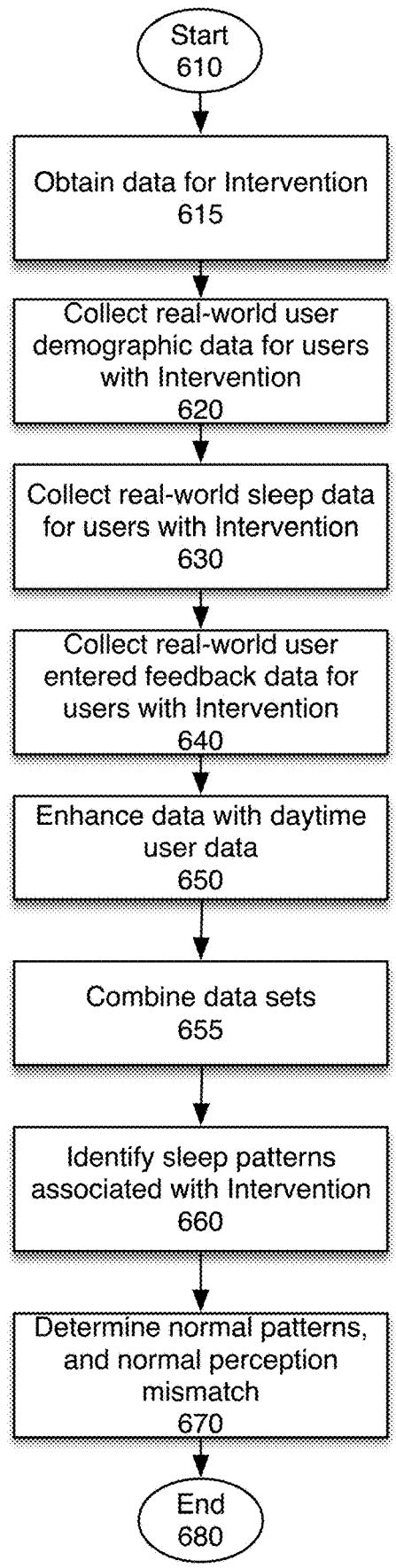
FIG. 6 is a flowchart of one embodiment of global effectiveness tracking for various medical interventions.

FIG. 6 is a flowchart of one embodiment of global effectiveness tracking for various medical interventions. The process starts at block 610. This type of pattern data may be analyzed for drugs such as opiates, sleep assistance drugs, drugs addressing breathing issues such as COPD, or any other drug that may have an impact on sleep. This type of data may also be corrected for the use of certain machines, such as CPAP and BiPAP machines. This type of data may also be accumulated for surgical interventions, such as implantation of a breathing assistance apparatus, At block 615, drug data is obtained for Intervention A. In one embodiment, the intervention data obtained includes the changes in wakefulness, pain control, and other impacts of the intervention on the human body.

At block 620, demographic data is collected for the real-world users. The demographic data includes gender, age, health issues, etc.

At block 640, real-world sleep data is collected from the users utilizing intervention A. In one embodiment, real world sleep data is collected over time. While the data collection is anonymized for analysis and any aspect not tied to the individual user, in one embodiment, the system does associate the user's characteristics with their data. Thus, for example, the system can distinguish between the sleep impact of a drug on men v. women, children v. adults, older people v. younger people, etc. In one embodiment, any available demographic characteristic may be separated out.

At block 640 user feedback data is collected. This process flow is parallel to the one described above for data collection for analysis for the user. While this is illustrated separately, one of skill in the art would understand that this is the same data set collected to evaluate the user's compliance status.

At block 650 in one embodiment the sleep data is enhanced with daytime user data, when available. The daytime user data provides information about the user's energy level and movement during the day.

At block 655, the data sets are combined. The data sets include the real world sleep data, the user entered feedback, the daytime user data, if appropriate.

At block 660, the process identifies sleep patterns associated with intervention A. In one embodiment, the sleep patterns are associated with intervention A based on the patterns being different from the baseline patterns for users with the same characteristics. In one embodiment, the sleep patterns that are identified are stored.

At block 670, the normal patterns and normal perception mismatch are identified based on large data sets. In one embodiment, The process then ends at block 680.

Note that although FIG. 6 is in a flowchart format the data collection order is not linear but rather data is collected from various sources continuously and updated. Thus, while the system is illustrated as a flowchart it is not ordered, but rather data is received and processed, in any order. In one embodiment, the process accumulates a set of data, and then reprocesses the complete set of available data.

Figure 7:
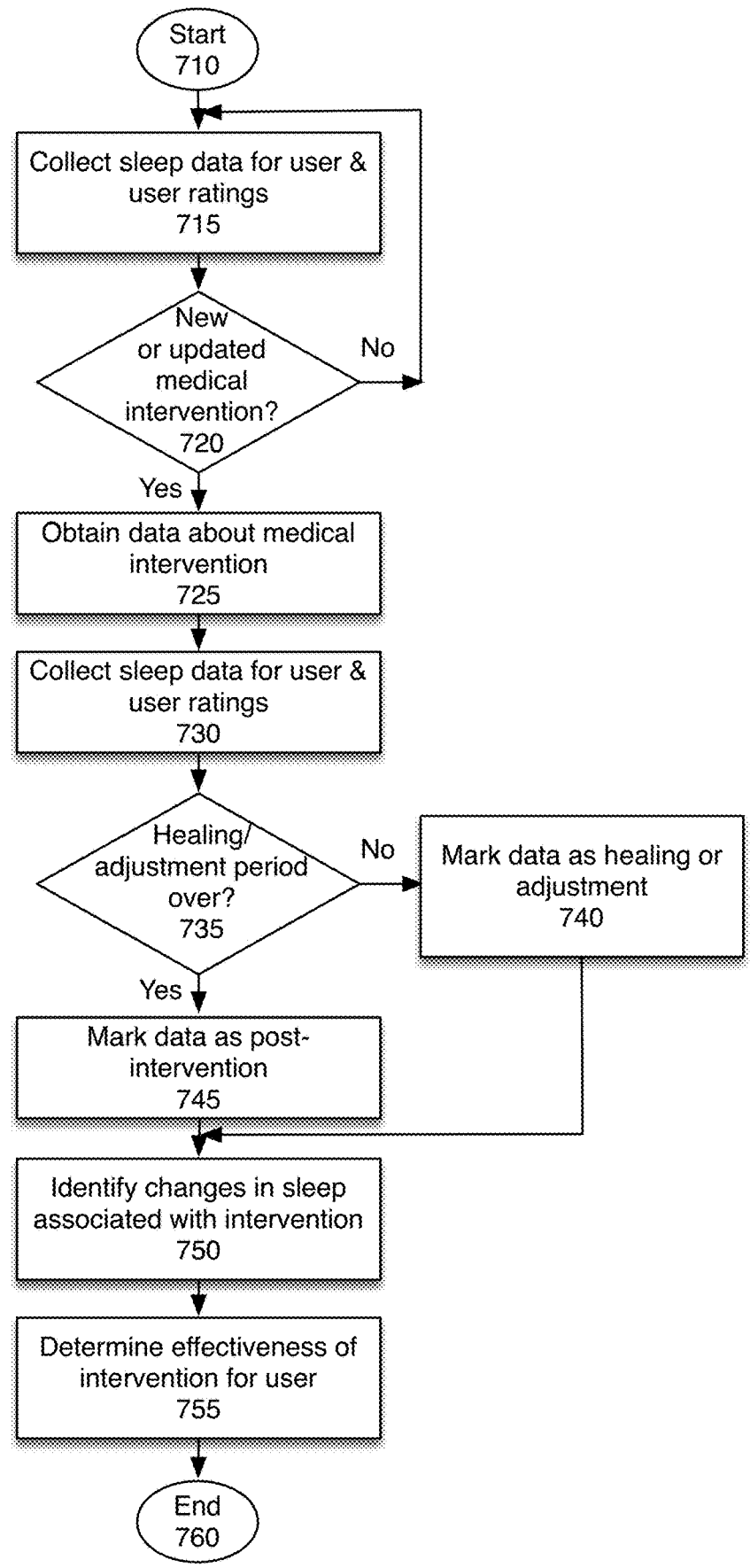
FIG. 7 is an overview flowchart of one embodiment of effectiveness tracking.

FIG. 7 is an overview flowchart of one embodiment of effectiveness tracking. The process starts at block 710.

At block 715, user sleep data is obtained, and tracked over time. This is a baseline data collection which may occur with or without existing medications or medical interventions to assist the user's sleep.

At block 720, the process determines whether there is a new or updated medical intervention. A new medical intervention may be a new apparatus such as a CPAP/BiPAP machine, a new surgical intervention such as an implant of a breathing assistance system, a new medication, etc. An updated medical intervention may be an adjustment in the dosage or setting of the intervention being currently used.

At block 725, the system obtains data about the medical intervention. In one embodiment, this data may be obtained directly from the user, or from a medical provider. In one embodiment, the user may for example take a picture of a new prescription or device setting, and the system may utilize that to create the new medical intervention or adjust the existing medical intervention.

At block 730, the system collects sleep data for the user, and user ratings, as previously. In one embodiment, there is no change in the data collection mechanism.

At block 735, the process determines whether the healing or adjustment period is over. For many medical interventions, the initial period after starting the use of a new medication or machine, or after surgery, there is a period for healing and adjusting to the new normal. If the healing/adjustment period is not yet over the data is marked as such, at block 740. Otherwise, the data is marked as post-intervention at block 745. This enables adjustment of the tracking for initial issues. Furthermore, it allows the doctor and/or manufacturer to focus on the healing period separately in evaluating the impact of the medical intervention.

At block 750, the changes in the sleep of the user associated with the intervention are identified. In one embodiment, this is done when there is sufficient pre-intervention data and post-intervention data for the user. For users that did not have pre-intervention data, the system can only track changes associated with adjustments and healing.

At block 755, the process determines the effectiveness of the intervention for the user. The effectiveness may be determined based on sleep quality. The effectiveness may also be determined based on a reduction or elimination of respiratory events while the user sleeps. If there is no pre-intervention data, effectiveness of the intervention may be determined based on sleep quality and respiratory event frequency of the user, post intervention, compared to statistical data for other users with similar user characteristics.

The process then ends at block 760. In one embodiment, this data may be shared with the medical provider, user, and manufacturer. In this way, the system, by providing continuous monitoring enables optimizing of outcomes for patients.

Figure 8:
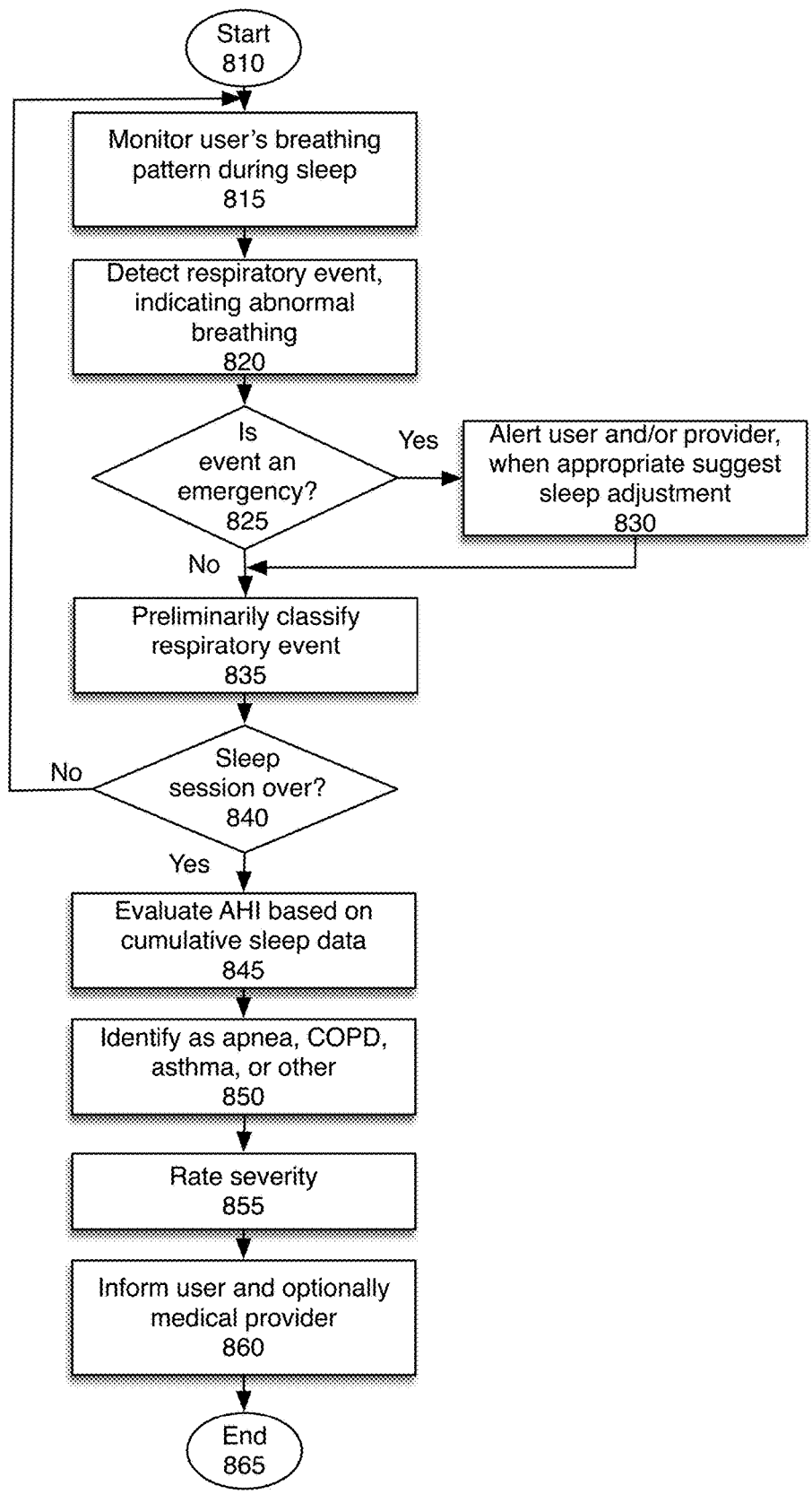
FIG. 8 is a flowchart of one embodiment of classifying a sleep incident.

FIG. 8 is a flowchart of one embodiment of classifying a sleep incident. The process starts at block 810. At block 815 the user's breathing, heart rate, and sleep sounds are monitored during a sleep session.

At block 820, a respiratory event is detected. A respiratory event is a period of abnormal breathing during sleep.

At block 825, the process determines whether the event is an emergency. An emergency event is one where the user is not taking in enough oxygen to continue functioning properly. An apnea event longer than 60 seconds, for example, may be considered dangerous. If the event is an emergency, the user is alerted in one embodiment. In one embodiment, the medical provider for the user may also be alerted. In one embodiment, in severe cases which are predicted to lead to permanent harm, the system may alert emergency services.

Once the user is awake, in one embodiment, the system may suggest that the user change their sleeping environment, and contact their medical provider. The process continues to block 835.

If the event is not sufficiently severe to be deemed an emergency, the process continues directly to block 835.

At block 835, the process preliminarily classifies the respiratory event. In one embodiment, the classifications include apnea, COPD, and asthma. Other classifications may be added.

At block 840, the process determines whether the sleep session is over. If not, the process returns to block 815 to continue monitoring. Once the sleep session is over, the process continues to block 845.

At block 845, the process evaluates the apnea-hypopnea index (AHI) for the user. The classification and severity of obstructive sleep apnea is traditionally based on apnea-hypopnea index (AHI). In general, an AHI of fewer than five events per hour is judged as normal, between five and fifteen events per hour is mild, fifteen to thirty events are moderate, and more than thirty are considered severe. However, utilizing a combination of AHI and per-event duration provides a clearer picture of the impact of the event. In one embodiment, the AHI evaluation is therefore supplemented by an evaluation of the length of each of the apnea events.

Based on the AHI and the preliminary classification, the system identifies the respiratory event, at block 850, and rates its severity at block 855.

At block 860, the user is informed, and optionally so is the medical provider. In one embodiment, the system may recommend mitigations or adjustments to the existing medical interventions to address the respiratory evens, if they are severe. The process then ends at block 865.

Figure 9:
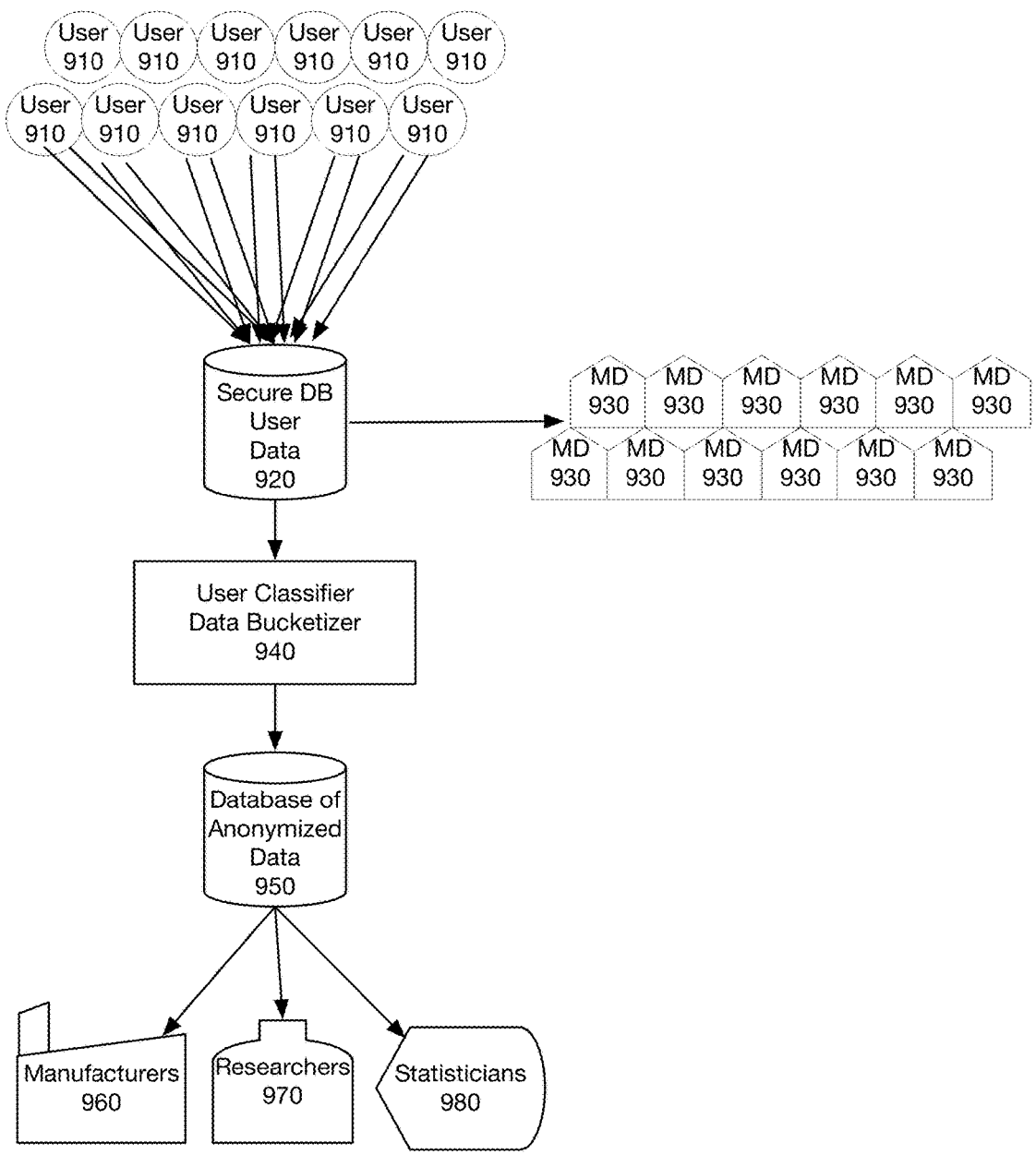
FIG. 9 is a diagram illustrating the provision of data sets.

FIG. 9 is a diagram illustrating the provision of data sets. Data is collected from a large number of users 910. The data collected includes personal data (e.g. each user's age, gender, health status, etc.) as well as medications taken, medical interventions used, etc. This data is securely stored in secure database 920, for user data. The individual medical providers, MD 930, have access to each data set from their own patients. In one embodiment, a simplified dashboard is presented to the medical provider, showing the condition of each of their patients. In one embodiment, the color coding described above may be used to direct attention to those patients who likely need intervention for their health.

The user data 920 is passed to user classifier/data bucketizer (UCDB) 940. The UCDB 940 creates a data set which removes the user personal data, and instead creates "buckets" of similar users whose data is aggregated. This ensures that the data cannot be disaggregated. In one embodiment, there are layers of buckets, e.g. a user may be in the "age 30-40, male, healthy" bucket, and simultaneously be in an "age 35, male, Philips Respironics CPAP user" bucket.

The resulting anonymized data is stored in database 950. This database in one embodiment may be made available to manufacturers 960. In one embodiment, manufacturers 960 may be given access to data buckets associated with their devices or drugs.

This database in one embodiment may be made available to researchers 970. Researchers 970 may be able to use the large scale data to analyze the effect of various medical interventions and improve the functioning of the associated medical device and drug dosages. In one embodiment, data from researchers 970 may be input to the predictive logic machine learning system. The database 950 in one embodiment may be made available to statisticians 980. In one embodiment, it may be possible to reprocess data to create different buckets, based on requests from these data recipients.

In this way, manufacturers, researchers, and doctors have a continual way to update and improve solutions to breathing issues. Both are very important, patient/practitioner and manufacturer. By providing processed and relevant data the system enables a continuous improvement of medical interventions and provides a set of data to researchers that may drive future designs.

Although the present application described particular medical interventions—including CPAP/BIPAP, Inspire Medical implants, ENT procedures, and medications—one of skill in the art should understand that any other medical interventions, whether currently used or developed in the future, to improve the sleep of users may be incorporated into this process. Because 40% of people over the age of 50 have apnea and/or COPD, providing such an improvement to the functioning of these interventions is very useful.

Figure 10:
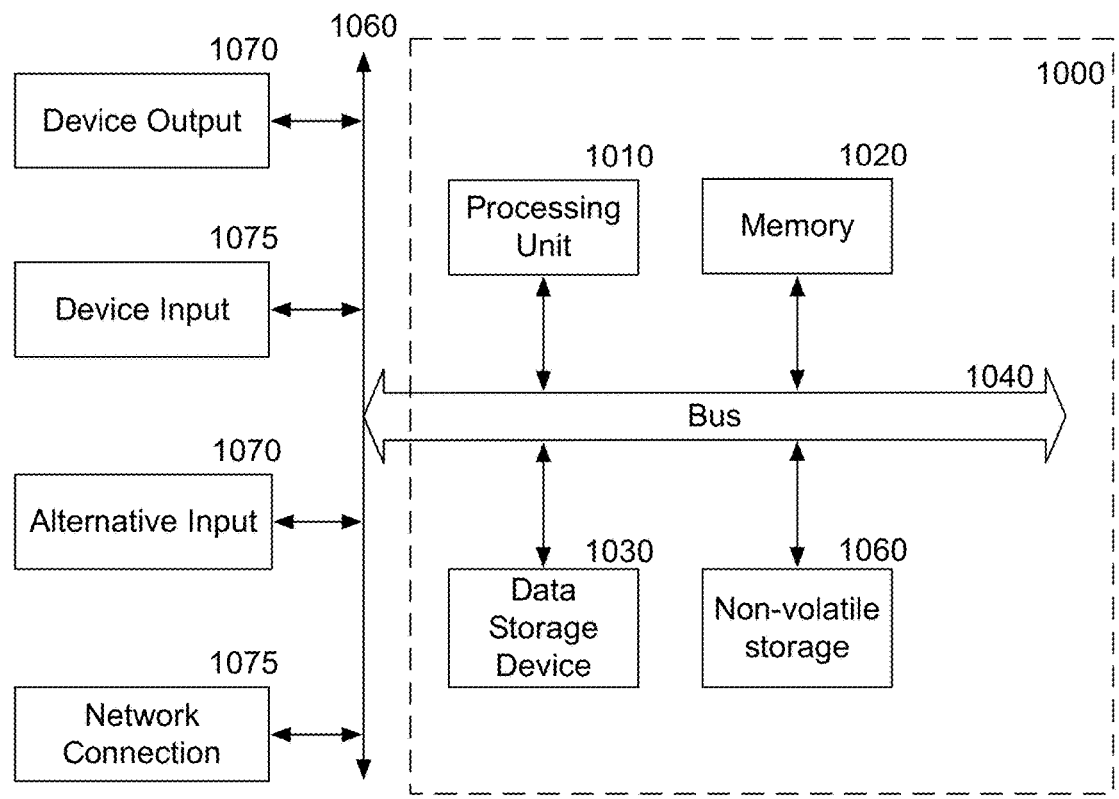
FIG. 10 is a block diagram of one embodiment of a computer system that may be used with the compliance and effectiveness tracking engine.

FIG. 10 is a block diagram of one embodiment of a computer system that may be used with the present invention. It will be apparent to those of ordinary skill in the art, however that other alternative systems of various system architectures may also be used.

The data processing system illustrated in FIG. 10 includes a bus or other internal communication means 1040 for communicating information, and a processing unit 1010 coupled to the bus 1040 for processing information. The processing unit 1010 may be a central processing unit (CPU), a digital signal processor (DSP), or another type of processing unit 1010.

The system further includes, in one embodiment, a random access memory (RAM) or other volatile storage device 1020 (referred to as memory), coupled to bus 1040 for storing information and instructions to be executed by processor 1010. Main memory 1020 may also be used for storing temporary variables or other intermediate information during execution of instructions by processing unit 1010.

The system also comprises in one embodiment a read only memory (ROM) 1050 and/or static storage device 1050 coupled to bus 1040 for storing static information and instructions for processor 1010. In one embodiment, the system also includes a data storage device 1030 such as a magnetic disk or optical disk and its corresponding disk drive, or Flash memory or other storage which is capable of storing data when no power is supplied to the system. Data storage device 1030 in one embodiment is coupled to bus 1040 for storing information and instructions.

The system may further be coupled to an output device 1070, such as a cathode ray tube (CRT) or a liquid crystal display (LCD) coupled to bus 1040 through bus 1060 for outputting information. The output device 1070 may be a visual output device, an audio output device, and/or tactile output device (e.g. vibrations, etc.)

An input device 1075 may be coupled to the bus 1060. The input device 1075 may be an alphanumeric input device, such as a keyboard including alphanumeric and other keys, for enabling a user to communicate information and command selections to processing unit 1010. An additional user input device 1080 may further be included. One such user input device 1080 is cursor control device 1080, such as a mouse, a trackball, stylus, cursor direction keys, or touch screen, may be coupled to bus 1040 through bus 1060 for communicating direction information and command selections to processing unit 1010, and for controlling movement on display device 1070.

Another device, which may optionally be coupled to computer system 1000, is a network device 1085 for accessing other nodes of a distributed system via a network. The communication device 1085 may include any of a number of commercially available networking peripheral devices such as those used for coupling to an Ethernet, token ring, Internet, or wide area network, personal area network, wireless network or other method of accessing other devices. The communication device 1085 may further be a null-modem connection, or any other mechanism that provides connectivity between the computer system 1000 and the outside world.

Note that any or all of the components of this system illustrated in FIG. 10 and associated hardware may be used in various embodiments of the present invention.

It will be appreciated by those of ordinary skill in the art that the particular machine that embodies the present invention may be configured in various ways according to the particular implementation. The control logic or software implementing the present invention can be stored in main memory 1020, mass storage device 1030, or other storage medium locally or remotely accessible to processor 1010.

It will be apparent to those of ordinary skill in the art that the system, method, and process described herein can be implemented as software stored in main memory 1020 or read only memory 1050 and executed by processor 1010. This control logic or software may also be resident on an article of manufacture comprising a computer readable medium having computer readable program code embodied therein and being readable by the mass storage device 1030 and for causing the processor 1010 to operate in accordance with the methods and teachings herein.

The present invention may also be embodied in a handheld or portable device containing a subset of the computer hardware components described above. For example, the handheld device may be configured to contain only the bus 1040, the processor 1010, and memory 1050 and/or 1020.

The handheld device may be configured to include a set of buttons or input signaling components with which a user may select from a set of available options. These could be considered input device #1 1075 or input device #2 1080. The handheld device may also be configured to include an output device 1070 such as a liquid crystal display (LCD) or display element matrix for displaying information to a user of the handheld device. Conventional methods may be used to implement such a handheld device. The implementation of the present invention for such a device would be apparent to one of ordinary skill in the art given the disclosure of the present invention as provided herein.

The present invention may also be embodied in a special purpose appliance including a subset of the computer hardware components described above, such as a kiosk or a vehicle. For example, the appliance may include a processing unit 1010, a data storage device 1030, a bus 1040, and memory 1020, and no input/output mechanisms, or only rudimentary communications mechanisms, such as a small touch-screen that permits the user to communicate in a basic manner with the device. In general, the more special-purpose the device is, the fewer of the elements need be present for the device to function. In some devices, communications with the user may be through a touch-based screen, or similar mechanism. In one embodiment, the device may not provide any direct input/output signals, but may be configured and accessed through a website or other network-based connection through network device 1085.

It will be appreciated by those of ordinary skill in the art that any configuration of the particular machine implemented as the computer system may be used according to the particular implementation. The control logic or software implementing the present invention can be stored on any machine-readable medium locally or remotely accessible to processor 1010. A machine-readable medium includes any mechanism for storing information in a form readable by a machine (e.g. a computer). For example, a machine readable medium includes read-only memory (ROM), random access memory (RAM), magnetic disk storage media, optical storage media, flash memory devices, or other storage media which may be used for temporary or permanent data storage. In one embodiment, the control logic may be implemented as transmittable data, such as electrical, optical, acoustical or other forms of propagated signals (e.g. carrier waves, infrared signals, digital signals, etc.).

In the foregoing specification, the invention has been described with reference to specific exemplary embodiments thereof. It will, however, be evident that various modifications and changes may be made thereto without departing from the broader spirit and scope of the invention as set forth in the appended claims. The specification and drawings are, accordingly, to be regarded in an illustrative rather than a restrictive sense.

We claim:

1. A compliance and effectiveness tracking engine system comprising:
   a sensor system to obtain sensed sleep data for a sleep session for a user;
   a user interface implementing a user data acquisition system to obtain perceived sleep data from the user after the sleep session;
   a server system implementing a predictive engine to generate predicted sleep data for the user, based on user background data and transactional data reflecting one or more medical interventions for the user;
   a server implementing a compliance and effectiveness tracking engine (CETE) to compare the sensed sleep data, the perceived sleep data, and the predicted sleep data, and to determine effectiveness of the one or more medical interventions for the user, and compliance with a protocol associated with the one or more medical interventions.

2. The system of claim 1, wherein the sensor system comprises one of: an accelerometer, a pressure sensor, a passive IR-sensor.

3. The system of claim 1, further comprising:
   a sleep analysis logic to: identify sleep phases through the sleep session, and to determine heart rate and breathing rate.

4. The system of claim 3, wherein the heart rate and the breathing rate are determined based on motion data from the sensor system.

5. The system of claim 1, further comprising:
   a respiratory event analyzer to identify a respiratory event during the sleep session, in near real-time;
   the respiratory event analyzer further to determine whether the respiratory event is an emergency; and
   a feedback system to provide an alert to the user, when the respiratory event is an emergency.

6. The system of claim 5, further comprising:
   the feedback system to provide data to the user about the effectiveness of the medical interventions.

7. The system of claim 5, further comprising:
   the respiratory event analyzer detecting abnormal breathing, and preliminarily classifying the respiratory event, and after the sleep session, calculating an apnea-hypopnea index (AHI), the AHI and the sensed sleep data used to classify the abnormal breathing as apnea, chronic obstructive pulmonary disease, or asthma.

8. The system of claim 7, wherein in addition to the AHI, the respiratory event analyzer utilizes a length of each respiratory event to identify the abnormal breathing.

9. The system of claim 1, further comprising:
   the server system to receive collected data including the sensed sleep data and the perceived sleep data from a plurality of users, and categorizing and bucketizing the collected data using user characteristics and the medical interventions;
   a data store storing the bucketized collected data from the plurality of users.

10. The system of claim 9, further comprising:
    the server system to anonymize the data in the data store, and provide an interface to make the anonymized data available to manufacturers and researchers.

11. The system of claim 1, further comprising:
    the server system to determine when the predicted sleep data and the sensed sleep data are different, and flag the difference as it is an indicator that the user is not complying with the protocol associated with the one or more medical interventions.

12. The system of claim 1, wherein the one or more medical interventions include one or more of: opioids to address pain, sleep medication, continuous positive airway pressure (CPAP) ventilator, bilevel positive airway pressure (BiPAP) ventilator, an implanted medical device, and surgery.

13. The system of claim 12, wherein the protocol associated with the medical interventions comprises:
    dosage and timing for the opioids and for the sleep medication;
    usage of and settings for the CPAP ventilator and the BiPAP ventilator;
    usage of the implanted medical device.

14. The system of claim 1, further comprising:
    the server to collect the sensed sleep data for the user prior the medical intervention, and after the medical intervention; and
    the CETE to utilize changes in the sleep data to determine effectiveness of the medical intervention.

15. The system of claim 14, further comprising:
    the server to receive data regarding a healing or adjustment period for a user, and the server to separately analyze the medical intervention during the healing or adjustment period.

16. A method of tracking compliance with a medical protocol for a medical intervention and effectiveness of the medical intervention, the method comprising:
    collecting sensed sleep data for a sleep session for a user;
    obtaining perceived sleep data from the user after the sleep session;
    calculating predicted sleep data for the user, based on user background data and transactional data reflecting the medical intervention for the user;
    comparing the sensed sleep data, the perceived sleep data, and the predicted sleep data, to determine effectiveness of one or more medical interventions for the user, and compliance with the medical protocol associated with the one or more medical interventions.

17. The method of claim 16, wherein the one or more medical interventions and associated medical protocols are:
    dosage and timing for opioids to address pain, and for sleep medication;

usage of and settings for a continuous positive airway pressure (CPAP) ventilator and a bilevel positive airway pressure (BiPAP);
usage of an implanted medical device; and
healing protocols for surgery.

18. The method of claim 16, further comprising:
identifying a respiratory event during the sleep session, in near real-time;
determining whether the respiratory event is an emergency; and
alerting the user, when the respiratory event is an emergency.

19. The method of claim 18, further comprising:
preliminarily classifying the respiratory event in near real-time;
after the sleep session, classifying each of the respiratory events and calculating an apnea-hypopnea index (AHI); and
using the AHI and a length of each respiratory event to classify the respitory event as apnea, chronic obstructive pulmonary disease, or asthma.

20. A compliance and effectiveness tracking engine system comprising:
a sensor system to obtain sensed sleep data for a sleep session for a user;
a sleep analysis system to identify sleep phases, during the sleep session, and to identify respiratory events occurring during the sleep session, an output of the sleep analysis system being processed to determine sensed sleep data, including a sleep score, waking and sleeping times, sleep duration, deep and REM sleep ratios, and wake-ups;
a user interface implementing a user data acquisition system to obtain perceived sleep data from the user after the sleep session, the perceived sleep data including when the user went to sleep, when the user woke up, how often the user woke during the sleep session, and a restfulness of the sleep session;
a server system implementing a predictive engine to generate predicted sleep data for the user, based on user background data and transactional data reflecting one or more medical interventions for the user, and medical protocols associated with the one or more medical interventions;
a server implementing a compliance and effectiveness tracking engine (CETE) to compare the processed sensed sleep data, the perceived sleep data, and the predicted sleep data, and to determine effectiveness of the medical intervention for the user, and compliance with the medical protocol associated with the medical intervention.

* * * * *